United States Patent [19]

Spina et al.

[11] 4,078,564
[45] Mar. 14, 1978

[54] INTRALENTICULAR CATARACT SURGERY

[75] Inventors: Joseph Spina, Bryn Mawr; Michael K. Weibel, Philadelphia, both of Pa.

[73] Assignee: Novo Enzyme Corporation, Mamaroneck, N.Y.

[21] Appl. No.: 660,873

[22] Filed: Feb. 24, 1976

[51] Int. Cl.² .................. A61F 9/00; A61M 1/00; A61K 37/48
[52] U.S. Cl. .................... 128/216; 128/276; 128/303 R; 424/94
[58] Field of Search ............... 424/94; 128/1 R, 213, 128/215, 216, 276, 303 R; 175/2

[56] References Cited

U.S. PATENT DOCUMENTS 3,320,131  5/1967  Smith ........................ 424/94
3,589,363  6/1971  Banko et al. ................. 128/276

Primary Examiner—Channing L. Pace
Attorney, Agent, or Firm—Fidelman, Wolffe & Waldron

[57] ABSTRACT

An enzymatic intralenticular cataract treatment for removal of nuclear cortical and subcapsular regions of the cataractous lens through enzymatic digestion thereof which comprises introduction of a concentrated solution of mixed exogenous enzymes into the nuclear and cortical regions of a cataractous lens, and after enzymatic digestion removing the liquefied cataractous material. The procedure allows removal of the nuclear, cortical and subcapsular portions of a cataractous lens through a very tiny incision in the eye and lens capsule, leaving all other structures within the eye intact.

5 Claims, 3 Drawing Figures

INTRALENTICULAR CATARACT SURGERY

BACKGROUND OF THE INVENTION

I. Field of the Invention

This invention lies in the field of cataract surgery and in particular relates to the enzymatic treatment of cataracts followed by removal of the enzymatically digested cataractous material.

II. Background

The lens is an optically clear encapsulated disc-like structure which is suspended within the eye, behind the iris and in front of the vitreous. It supplies part of the optical refracting power of the eye. The lens becomes cataractous when it nuclear and/or cortical and/or subcapsular regions become opaque, thus blocking the path of light entering the eye, thereby causing diminished vision. A cataract is simply a lens that has become cloudy.

There are, generally speaking, two types of cataracts, congenital and senile. Congenital cataracts, approximately 1% of all cases, are found in people under the age of 25 and characteristically are relatively soft. Senile cataracts, approximately 99% of all cases, are found in older people and characteristically are relatively hard.

The Egyptians, who are believed to be the first to record treatment of cataracts, removed them by thrusting a rose thorn through the cornea and simple pushing the cataract back and down into the vitreous of the eye.

The next major procedure, one popular in the 1800's, took advantage of the fact that as a senile cataract develops it becomes more dense and cloudy, but after a number of years it becomes ripe, i.e. soft and liquid. The ripe or mature cataract was removed by making an incision in the eye near the cornea, cutting the anterior capsule and flushing the soft material out. It was not uncommon for the eye to become severely inflamed and, in addition, several operations were sometimes necessary to remove all lens debris. The greatest disadvantage of this procedure is that the patient could be blind for 10–20 years waiting for his or her cataract to become ripe.

The intracapsular technique of cataract surgery developed in the 1930's calls for making a large incision, 25 mm, approximately 180° around the cornea for an entry into the anterior chamber of the eye. After breaking the suspensory ligaments which suspend the lens within the eye, the lens is removed by mechanical means such as forceps or suction. Removal of the lens may be facilitated by the use of alpha chymo-trypsin to dissolve the ligaments that attach the lens to the ciliary body (the zonules). The advantage of this technique is that a patient no longer has to wait years for the cataract to become ripe. Several disadvantages exist. The large incision in a relatively sensitive organ requires multiple stitches to close. The removal of any barrier holding the vitreous body in place makes physical activity impossible for several days after the operation since the vitreous can then become displaced. The sensitivity of the eye structure can result in significant damage to the iris, retina, etc. However, the intracapsular technique is the most common procedure practiced and it is estimated that heretofore well over 360,000 of such procedures have been carried out each year in the U.S. alone.

Another method of surgery currently practiced is applicable only to congenital cataracts. If the cataract is extremely soft and liquid, the surgeon enters the anterior chamber of the eye through a small incision, then breaks the lens capsule and aspirates the contents thereof out using a 18 gauge needle and a normal syringe. If the lens is a little too hard to be aspirated in this manner, the surgeon makes several incisions in the anterior capsule and allows the aqueous humour of the anterior chamber at attack and hydrolyze the cataract. After several days the lens becomes soft enough to allow the above mentioned aspiration technique to be employed. This procedure works only for soft congenital cataracts and is not effective for senile cataracts because of the hardness of the lens material. Also, the surgeon cannot cut open a senile cataract and then wait (a long period) for the natural enzymes to work since the eye soon becomes severely inflamed due to the reaction of the lens material with the vascularized areas of the eye.

The object of this invention is to provide a procedure which eliminates much, if not all, of the hazards and trauma involved in the above described and other known cataract surgical procedures.

SUMMARY OF THE INVENTION

This invention provides a procedure for intralenticular cataract therapy which involves dispersing a concentrated mixture of exogenous enzymes throughout the nuclear, cortical and subcapsular regions of a cataractous lens. After a suitable period of time, e.g. 12–48 hours, the enzyme digested cataractous lens material is removed by aspiration and irrigation techniques.

RATIONALE OF THE INVENTION

The invention takes advantage of a unique physiological situation within the lens itself. During the embryonic stages of human development the lens material is isolated from the rest of the body and develops independent of the organism as a whole to such an extent that every human will react to the contents of his or her lens as if it were a foreign protein. In the adult human, the lens is surrounded by the lens capsule which is primarily collagen, and this capsule or bag actually isolates the lens from the body to such an extent that exogenous enzymes may be introduced into the lens without creating immunologic foreign protein responses thereto.

Technological advances have made available to the surgeon both equipment and techniques for operating on the lens itself. Conventional surgical equipment, including for example the operating microscope that has gone into wide spread use in the past 15 years now enable the surgeon to see details that previously were too small for visualization. In addition, the availability of micro cannulae make it possible for a surgeon to enter a structure as small as the human lens (approximately 9 mm in diameter) without doing major damage thereto. In total, the operating techniques and the surgical equipment required for surgery on the lens itself are available to the art, forming no part of this invention and will not be described herein (aside from allusions thereto when exemplary preferred emdobiments of practice of this invention are provided).

As is well know, the catabolism (breakdown) of whole cells and tissues begins with the degradation of their external membrane and connective structural components. The relevant chemistry is modulated by highly specific biological catalysts (called enzymes). Virtually every chemical reaction of the biological spectrum can be associated with an enzyme which catalyzes only that reaction. Significant biological precedent exists for belief that selective degradation of tissue and other complex biochemical elements at the cellular level can be attained. The multi-cellular organism itself degrades necrotic cells to relatively simple soluble biochemical components and re-employs these compounds for synthesis of new cells or for other metabolic functions. While the regulation and control of potent lytic enzymes within single cell or multi-cellular organisms is not totally understood, the general strategy employed by nature concerning these substances is known. In the instance of cataracts, the cataract ripening phenomena alluded to above offers hope that enzymatic digestion of senile cataracts might in fact be induced, and the isolation of the human lens from the body as a whole suggests that foreign body (immunologic) reactions to exogenous enzymes will not occur, if such enzymes are compartmentalized within the len capsule.

Within the art of opthalmic surgical intraocular procedures for conventional cataract removal, the use of an exogenous enzyme to facilitate the removal of an intact lens is established. A well characterized proteolytic enzyme, α-chymotrypsin, has been used to soften the suspensory ligaments of the zonular region which attach the lens capsule to the ciliary muscle.

Also the use of an exogenous enzyme, fibrinolysin, to degrade blood clots within the eye is established within the art of ophthalmic intraocular surgery.

Furthermore, there is an established precedent in the medical arts for use of digestive enzymes as an aid of necrotic tissue removal for wound debridement procedures.

In the treatment of congenital cataracts, too firm to be aspirated using a simple needle and syringe, some eye surgeons have believed for years that incision of the anterior capsule permits the enzymes for the aqueous humor to enter the firm nucleus, and then within a few days the cataract softens to the extent that it can be aspirated easily. This procedure does not work for hard, senile cataracts because of low peripheral permeability associated with their compact nature.

It has now been discovered that senile cataracts can be treated by exogenous enzymes, such as bacterial enzymes, so as to soften the lens sufficiently to allow its removal by apiration and irrigation techniques.

EXPLANATION OF THE INVENTION

For further understand of this invention, reference is now mde to the attached drawing, wherein:

FIG. 1 diagrammatically illustrates a cannula inserted in the lens of an eye.

Figure 3:
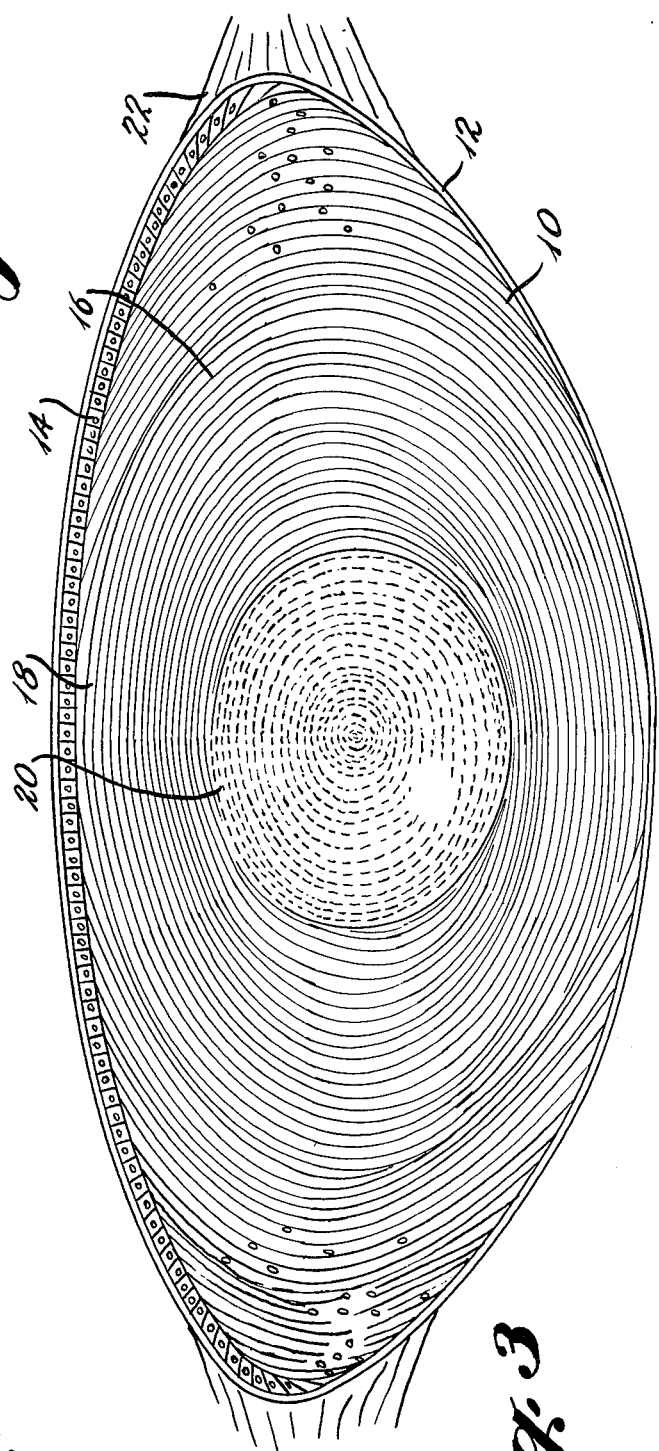
FIG. 3 is an enlarged diagrammatic cross-section of the human lens capsule and its contents.

Referring now to FIG. 3, it may be seen how the lens 10 is divided up into capsule 12 epithelium 14 and lens substance 16 which consists of lens fiber. The lens substance can be further described as made up of the cortex 18, the cortex being a layer of soft, young superficial fibers which lie directly beneath the capsule 12, and the nucleus, the nucleus 20 being the hard, closely packed cells at the center of the lens. Extending into lens 10 at the sides thereof are the zonules 22, the zonules being the suspensatory ligaments which retain the lens in place inside the eye.

Any exogenous material inserted into the lens can be physically compartmentalized within the lens substance 16 by the lens capsule 12, provided the material does not act destroy or rupture the lens capsule. If the opening made for insertion of the material is sealed, such material can be made to remain within the lens capsule 12 for an extended period of time. Significant to practice of this invention is that lens capsule 12 has a biochemical composition which is substantially different from that of cortex 18 and nucleus 20 of the main lens substance. Exogenous enzymes that are capable of selectively digesting the tissue of nucleus and cortex yet leave lens capsule 12 whole exist. Parenthetically it may be noted that the macromolecular character of enzymes keeps them from permeating rapidly, if at all, through the reticular structure of the capsular membrane. Accordingly, selective enzymes introduced into the cortex and nucleus will become trapped therein, and over a period of time are capable of enzymatically degrading the senile lens substance.

Figure 1:
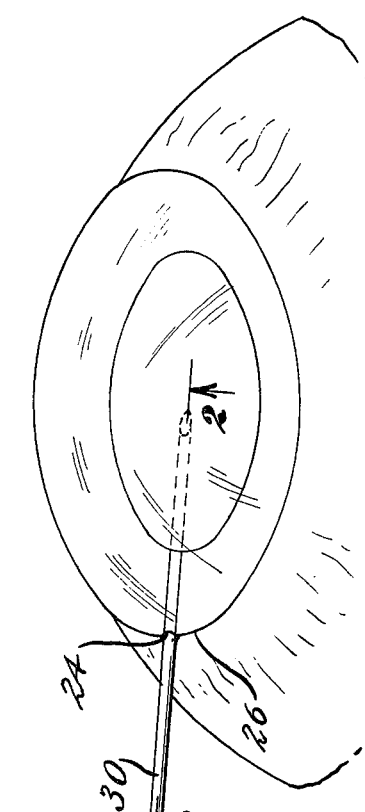

One exemplary mode of practicing the invention involves making a puncture 24 at the sclera or at the scleral-corneal juncture 26 large enough for a needle, as is illustrated in FIG. 1, followed by introduction of a concentrated solution of exogenous enzymes. Thereafter the opening is sealed, e.g. by an air bubble, and then sufficient time allowed for enzymatic digestion of the lens. Subsequently the liquefied lens is removed by conventional aspiration and irrigation techniques, employing for example the techniques described in the medical literature for removing congenital or soft cataracts. Desirably, cataract removal is carried by aspirating and irrigating through the already existing puncture opening 24.

As can be seen in FIG. 3, nucleus 20 and cortex 18 which completely fill the lens capsule, are layered (somewhat like an onion) so that any enzyme containing liquid forced into the lens substance 16 permeates the entire lens largely along the layer lines. In terms of practicing this invention the layered structure places virtually all of the cells in the nucleus and cortex into immediate contact with the enzymes in the liquid. A normal senile cataract will accommodate up to 20 microliters of liquid without increasing the intraocular pressure to a level where rupture of the capsule 12 occurs. Accordingly, introduction of a concentrated solution of exogenous enzymes directly into the lens according to practice of this invention focuses an enzymatic action exclusively upon cortical, nuclear and subcapsular cataractous material in vivo.

Degrading the cataract in situ as is herein contemplated imposes requirements for high levels of enzymatic unit activity and of selectivity. Fortuitously, highly selective enzymes are known to the art. In fact, several classes of exogenous enzymes are known to degrade selectively tissue components similar to those found in the human lens. They are lipases, proteases and glycolytic enzymes which respectively degrade various types of lipids, proteins and polysaccharids. With high purity forms of enzymes, such as for example in crystalline enzymes, concentrated (aqueous) solutions of mixed enzymes can be formulated, for example 10% wt/wt solutions. Accordingly, the above described 20 microliter limit allows introduction of as much as 2 mg of pure enzyme into the lens substance. Since a normal lens will weigh about 200 mg, the enzyme to substrate ratio of about 1:100 readily obtainable constitutes a high enzyme:substrate ratio particularly since the layered nature of the lens places virtually all of the lens cells into essentially direct contact with the enzyme solution. Exact preferred concentrations and enzymes cannot be provided. Basically, no ranges for enzyme concentration can be provided other than a general statement that concentrated solutions should be employed. If enzyme concentration is not high, digestion of the lens substance requires more time, and mechanical removal of the lens (cortex) residue may be required. On the other hand, the more concentrated enzyme solutions will digest the lens substance more rapidly and to a greater degree. High enzyme concentrations do not cause adverse results. During the course of the period allowed for digesting the lens substance, the protease auto-digest itself and digest the other enzymes as well. The exogenous enzymes will become deactivated within a few days, and by then the (softened or liquefied) cataractous lens is ripe for removal.

DETAILED PRACTICE OF THE INVENTION

Figure 2:
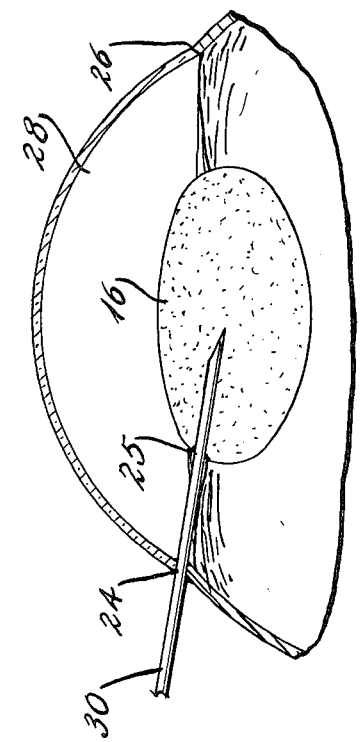
FIG. 2 is a cross-section taken along line 2—2 of FIG. 1.

The detailed practice of this invention can be appreciated in light of the drawing, notably of FIGS. 1 and 2. As can be seen therein, the lens degrading agent is delivered by a microcannula 30 attached to a suitable miniaturized liquid dispensing device such as a microliter syringe 32 from a scleral or scleralcorneal juncture puncture directly into nucleus 20, introducing for example 15 microliters of a 5% wt/wt enzyme solution. The outside diameter of the microcannula for example may be approximately 200 microns, or as small as structural strength considerations permit (The tip may be electronically tapered.) Large diameter cannulas tend to rent and/or rip the lens capsule during pentration thereof and substantially small diameter canulas do not possess sufficient rigidity to cleanly penetrate into the lens substance. Use of a tracked micromanipulator to reduce lateral motion of the cannula upon entering the lens is recommended, but is not considered essential. With the aid of an operating microscope, a 200 micron microcannula can be adequately inserted into the center of the lens manually. (Complete restriction of lateral motion by the cannula once positioned in the lens is essential, however, for maintaining a good seal about the needle track.)

As has already been pointed out, the enzyme containing solution injected into the lens by a manual or pneumatic driven syringe system is an amount of fluid which can be accommodated by an average human lens, i.e. not more than about 20 microliters. The distribution pattern of the injected fluid may be observed by incorporating a soluble, inert dye such as dichloroindophenol or a fluorescent dye such as fluorescein into the injection fluid.

In a preferred mode of enzyme introduction, injection of the solution into the central portion of the lens is followed by injection of a tiny air bubble into the track of the cannula as the cannula is withdrawn from the lens and out of the eye. This tiny air bubble serves to seal the small puncture site 25 in the lens capsule and thus to block the egress of enzyme solution from the lens (before normal intralenticular pressure is restored).

The composition of the digestive mixture and the intralenticular incubation time can be adjusted to achieve a high level of liquefaction or softening of the lens nuclear and cortical region. Termination of the lens liquefaction process and protection of other intraocular structures, in the event of escape of the enzymatic digestive agent from the lens capsule can be achieved by introduction of specific enzyme inhibitors into the anterior chamber 20 of the eye.

Contemplated for practice of this invention is introduction of enzyme inhibitors into the anterior chamber 28 of the eye in the event of enzyme leakage thereinto, or even as a precaution against such leakage. High molecular (or macromolecular) inhibitors will not permeate into the lens capsule, and therefore do not interfere with the enzymatic digestion of the lens cortex and nucleus. Low molecular weight inhibitors can diffuse through the lens capsule and may be used to terminate enzymatic digestion, both external and internal to the lens itself.

The exogenous enzymes found to be most effective for degrading cataractous lens tissue have been isolated from nonhuman sources and are not, in general, immunologically compatible with the human system. Therefore, these (enzyme) proteins are likely to be highly antigenetic. Fortunately, the lens is not vascularized and does not communicate with the immunological response machinery in mammals. Human lens proteins are themselves antigenic, indicating their early immunochemical isolation during cell differentiation. Accordingly, introduction of foreign proteinaceous substances into the lens, including digestive enzymes, does not cause adverse immunological reactions.

Since the biochemical composition of a large portion of the nuclear, cortical and subcapsular cataractous material is proteinaceous in character, a substantial number of proteolytic enzymes obtained from microbial, plant and animal sources have been screened for their ability to digest hard, senile human cataracts. Microbial proteases, preferably a mixture of diverse proteases, have been found the most satisfactory.

The other major biochemical components found in cataractous tissue are membrane constituents which, in addition to their protein elements, contain significant quantities of lipids, triglycerides and fatty acid esters. For this reason, the digestive enzyme mixture introduced into the lens includes also a phospholipase and a lipase, both of which have been found to enhance overall digestive action substantially.

The enzymatic mixture introduced into the lens will be a 0.1–10% wt/wt aqueous solution of the enzymes, desirably in saline buffered to pH 7.4, although pyrogen free distilled water might be employed. Crystalline ultra pure enzymes are of course preferred, but in practice somewhat lower purity level enzymes may be all that is available. No preferred enzyme mixture or proportions can be provided, except that the mixture should include at least two different proteases and a lipase and a phospholipase. For optimum results inclusin of still other enzymes may be found desirable. An exemplary enzyme mixture is described below.

After the concentrated 0.1–10% wt/wt enzyme solution has been introduced into the lens cortex, a suitable digestion period is allowed to elapse. Such period might for example be 3 days, and will depend upon enzyme concentration, the hardnes of the cataractous lens, even the preferences of the surgeon. Desirably, the lens will be liquefied to the point where the digested residue can be irrigated and aspirated out through the original cannula track into the lens. However, partial liquefaction such as size reduction and/or softening may satisfy the surgeon by allowing the senile cataract residue to be removed mechanically through a small (less than 180°) incision opening, or be fragmented then flushed out through a small incision opening. All in all, the enzyme concentration, the total quantity of liquid introduced into the lens, and digestion time may be varied to suit the requirements of the surgeon and the needs of the individual patient.

The invention is further illustrated by the following examples:

EXAMPLE 1

Enzymatic liquefaction of hard, senile cataractous human lenses.

Fresh, human, cataractous, whole lenses which had been surgically extracted on the day of the experiment were matched in size, color and hardness. The lens capsules were removed and each lens placed in a 2 ml volume of an enzyme containing incubation buffer. The buffer was a sterile-balanced salt solution, pH 7.4 (0.01 M potassium phosphate, 0.49% NaCl, 0.075% KCl, 0.048% $CaCl_2.2H_2O$, 0.030% $MgCl_2$). The control solution employed was simply the balanced salts buffer. The digestive solutions contain the following quantities of 3 proteases, 1 lipase and 1 phospholipase expressed as international units of catalytic activity per ml of incubation buffer; subtilisin BPN' protease — 250 units per ml, S. griseus — 75 units per ml. elastase — 120 units per ml, pancreatic lipase — 20,000 units per ml, and phospholipase from V. russelli venum — 75 units per ml, respectively.

Subtilisin BPN' and S. gresius proteases;

1 unit defined as that amount of enzyme which produces 1 μmole of TCA soluble tyrosine per minute (measured by standard Folin-Ciocalteau method) employing caesin as the substrate. The experimental conditions are 0.6% wt/vol caesin in 0.05 M $K_2HPO_4/KH_2PO_4$ pH 7.5 at 37° C.

Elastase;

1 unit defined as that amount of enzyme which solubilizes 1 mg elastin per 20 min (measured by spectrophotometric method) employing elastin-orcein as the substrate. The experimental conditions are 12 mg/ml elastin-orcein in 0.2 M $Tris/SO_4$ pH 8.8 at 37° C.

Lipase (hog pancreas);

1 unit defined as that amount of enzyme which hydrolyzes 1 μ equivalent of fatty acid per hour from a triglyceride (measured by pH stat method) employing an olive oil emulsion as the substrate. The experimental conditions are 50% vol/vol suspension of olive oil in 3 M NaCl containing 15 mg/ml taurocholate and 0.075 M $CaCl_2$ pH 8.0 at 37° C.

Phospholipase A (V. russelli);

1 unit is defined as that amount of enzyme which hydrolyzes 1 μmole L-α-phosphatidyl choline to L-α-lysophosphatidyl choline and a fatty acid per minute (measured by spectrophotometric method of Fe/hydroxylamine color reaction with products) employing lecithin as the substrate. The experimental conditions are 2 mg/ml lecithin in 0.05 M 2,4,6 collidine containing 0.005 M $CaCl_2$ pH 6.5 at 37° C.

The results obtained by incubation of whole lenses in this digestive medium were as follows: 24 hours incubation reduced the diameter of the lenses which were incubated in a digestive mixture by approximately one-half (½). After 48 hours the diameter of the lenses was approximately one-third (⅓) to one-fourth (¼) the size of the control lenses. After 72 hours the diameter of the lenses in the digestive mixture was approximately one-fifth (1/5) of the size of the control lenses. The control lense, incubated in the basic salts medium, showed no reduction in size or change in appreareance. Examination of the protease activity remaining in the supernatant of the digestive mixture after 72 hours, showed that the protease activity had been substantially reduced by autolysis and was without further activity with regard to degradation of lens material. Similar experiments, performed at 37° C, showed essentially the same degradation kinetics although the auto-inactivation of the enzymatic activity associated with autolysis appeared to be slightly faster.

EXAMPLE 2

Observation of the distribution of liquid injected into intact lenses, utilizing live animals and human eyebank eyes.

Three live rabbits (six eyes) and four fresh, human eyebank eyes were injected with an inert tracking dye (dichloroindophenol, using the microcannula and microliter syringe apparatus with visualization by surgical operating microscope. Injection of the dye into the central portion of the lens was followed by injection of a tiny air bubble into the track or opening left by the cannula as the cannula was withdrawn from the lens and out of the eye. This tiny air bubble served to seal the small puncture site in the lens capsule and thus block the egress of the dye from the lens. Direct visualization by the surgical operating microscope during this procedure confirmed that up to 20 microliters of liquid could be completely confined within the interior of the lens without leakage into the anterior or vitreous chambers and yet be well distributed throughout the nuclear, cortical and subcapsular areas of the lens. The rabbit eyes were then removed after sacrificing the animals. The rabbit eyes and the human eyebank eyes were then fixed, sectioned and examined histologically to confirm the results. Similar injection experiments were performed using intact cataractous lenses which had been extracted surgically on the same day of the experiment. The results, using these intact, cataractous lenses, were essentially identical both when visualized using the surgical operating microscope and when examined histologically.

EXAMPLE 3

Liquefaction of cataractous material utilizing intact, human, cataractous lenses; degradative enzyme mixture; and microcannula and microliter syringe injection system.

Intact, human, cataractous lenses surgically extracted on the same day of the experiment were injected with the degradative enzyme mixture of Example 1 (20 microliters). The degradative enzyme mixture was confirmed within the lens and was dispersed throughout the cataractous portion of the lens, in each case. Control lenses were injected with the balanced salt solution containing no degradative enzymes. After 72 hours the control lenses had undergone no digestion; however, the lenses injected with the enzyme degradative mixture demonstrated substantial digestion of the nuclear and cortical regions.

EXAMPLE 4 In Vivo Studies

In order to determine the amount of trauma, inflammation and other adverse response, which might result from introduction of the enzymes by the technique described above or by accidental escape of the enzymes into the anterior chamber, three (3) live cats (six eyes) received injection of the enzyme mixture into the lens with deliberate leakage of the enzyme mixture into the anterior chamber. One (1) eye of each cat was treated with 20 microliters of the enzyme mixture and the other with 20 microliters of inert tracking dye. Sterile technique was not used; however, each animal received a single, large dose of intramuscular Ampicillin immediately post-operatively. The eyes were examined daily for one week. One of the six (6) eyes rapidly developed purulent endophtalmitis resulting from the lack of sterile technique. There was no clinical sign of inflammation or destruction of extralenticular structures resulting from the presence of the enzymes in any of the remaining five (5) eyes. Normal intraocular pressure was present post-operatively.

ALTERNATIVE MODES

Although the previously described preferred practice of this invention specifies use of a mixture of rather selective enzymes, as a practical matter providing such a mixture or mixtures on large scale for wide spread usage presents probelms, and the very concept of liquefying or softening the lens with one enzyme is most attractive, i.e. with a protease alone.

In actuality the proteinaceous character of lens tissue allows a single strong exogenous protease, such as for example the protease from microorganisms like *B. subtilis* and *B. licheniformis* to soften or liquefy the lens, albeit less selectively than is possible with a mixture of selective enzymes. Use of one protease alone is contemplated, e.g. 500 units/ml in concentration, for practice of this invention.

One pecularity of many microorganisms employed for protease production (advantageous for purposes of this invention) is that a multiplicity of proteases is elaborated by the microorganism, and what is commonly offered as a purified single protease product constitutes a mixture of quite different proteases. Such a naturally occurring mixture would of course be suitable as the protease for liquefying or softening the cataract, alone or in admixture with other enzymes.

What is claimed:

1. A method for enzymatically treating cataracts in vivo which comprises injecting a concentrated solution of at least one exogenous lens digesting enzyme directly into the lens of an eye, then allowing enzymatic digestion of the lens to take place and thereafter removing the enzyme digested lens material.

2. The method of claim 1 including the step of injecting an enzyme solution including at least one protease, a lipase and a phospholipase.

3. The method of claim 1 including the step of injecting an enzyme solution including a multiplicity of proteases.

4. The method of claim 1 including the step of incorporating a tracking indicator in the enzyme solution.

5. The method of claim 1 including, after the step of injecting the enzyme solution the step of injecting an air bubble into the injection opening, sealing same against leakage of the enzyme solution from the lens.

* * * * *

REEXAMINATION CERTIFICATE (564th)

United States Patent [19]

Spina et al.

[11] B1 4,078,564

[45] Certificate Issued  Sep. 16, 1986

[54] INTRALENTICULAR CATARACT SURGERY

[76] Inventors: Joseph Spina, 767 Woodlea Rd., Bryn Mawr, Pa. 19010; Michael K. Weibel, 605 S. 48th St., Philadelphia, Pa. 19143

Reexamination Request:
No. 90/000,853, Sep. 11, 1985

Reexamination Certificate for:
Patent No.: 4,078,564
Issued: Mar. 14, 1978
Appl. No.: 660,873
Filed: Feb. 24, 1976

[51] Int. Cl.$^4$ .................. A61M 31/00; A61B 19/00; A61K 37/48; A61B 17/00
[52] U.S. Cl. .................. 604/51; 128/1 R; 424/94; 128/303 R
[58] Field of Search .................. 604/49, 51; 128/1 R, 128/303 R; 424/94

[56] References Cited
PUBLICATIONS

Middleton, J. M., *Journal of the International College of Surgeons*, 37, 66–84 (1962).
Bonnet, M. et al., *Bulletin des Societes d'Ophthalmologica de France*, 69, 583–586 (1969).
Klein, J. et al., *Acta Ophthalmologica*, 50, 215–228 (1972).

*Primary Examiner*—J. Yasko

[57] ABSTRACT

An enzymatic intralenticular cataract treatment for removal of nuclear cortical and subcapsular regions of the cataractous lens through enzymatic digestion thereof which comprises introduction of a concentrated solution of mixed exogenous enzymes into the nuclear and cortical regions of a cataractous lens, and after enzymatic digestion removing the liquefied cataractous material. The procedure allows removal of the nuclear, cortical and subcapsular portions of a cataractous lens through a very thin incision in the eye and lens capsule, leaving all other structures within the eye intact.

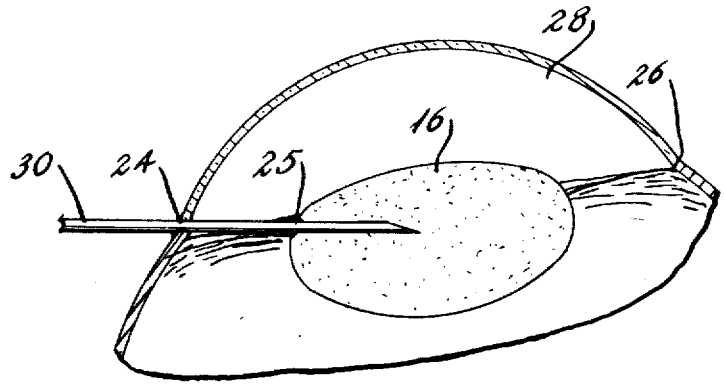

REEXAMINATION CERTIFICATE ISSUED UNDER 35 U.S.C. 307

THE PATENT IS HEREBY AMENDED AS INDICATED BELOW.

Matter enclosed in heavy brackets [] appeared in the patent, but has been deleted and is no longer a part of the patent; matter printed in italics indicates additions made to the patent.

AS A RESULT OF REEXAMINATION, IT HAS BEEN DETERMINED THAT:

Claims 1 and 5 are determined to be patentable as amended.

Claims 2-4, dependent on an amended claim, are determined to be patentable.

1. A method for enzymatically treating cataracts in vivo which comprises injecting a concentrated solution of at least one exogenous lens digesting enzyme directly into the lens of an eye, *confining the enzyme solution within the lens,* then allowing enzymatic digestion of the lens to take place and thereafter removing the enzyme digested lens material.

5. The method of claim 1, *wherein the step of confining the enzyme solution within the lens comprises* [including after the step of injecting the enzyme solution the step of] injecting an air bubble into the injection opening, sealing same against leakage of the enzyme solution from the lens.

* * * * *